United States Patent [19]

Sikkenga

[11] Patent Number: 4,642,301

[45] Date of Patent: Feb. 10, 1987

[54] HALIDED ALUMINA CATALYST

[75] Inventor: David L. Sikkenga, Wheaton, Ill.

[73] Assignee: Amoco Corporation, Chicago, Ill.

[21] Appl. No.: 792,902

[22] Filed: Oct. 30, 1985

[51] Int. Cl.$^4$ .............................................. B01J 21/04
[52] U.S. Cl. ..................................... 502/231; 585/533
[58] Field of Search ......................................... 502/231

[56] References Cited

U.S. PATENT DOCUMENTS 3,268,618 8/1966 Fletcher et al. ................. 502/231 X
3,395,187 7/1968 Christoph ........................ 502/231 X
3,449,264 6/1969 Myers .............................. 502/231 X Primary Examiner—Patrick P. Garvin
Attorney, Agent, or Firm—Matthew R. Hooper; William T. McClain; William H. Magidson

[57] ABSTRACT

Improved halided alumina catalysts are prepared by first calcining the gamma-alumina catalyst base at a temperature of 1300°–1800° F. The finished catalyst can be employed for olefin polymerization without need for refrigeration to control the exothermic heat of reaction.

7 Claims, No Drawings

HALIDED ALUMINA CATALYST

BACKGROUND OF THE INVENTION

This invention relates to an improved process for the manufacture of hydrocarbon conversion catalysts comprising halided aluminas. More particularly this invention relates to a novel high-activity chlorided alumina catalyst for use in the polymerization of mixed butene streams, containing substantial proportions of isobutene, to yield high-viscosity polybutenes.

Halided alumina catalysts have been used in a variety of hydrocarbon conversion processes, as diverse as isomerization, reforming and hydrofining, optionally combined with other catalytic agents. Such catalysts, for use in olefin polymerization, are extensively described in U.S. Pat. No. 4,288,649, which is expressly incorporated herein by reference.

A major problem in the polymerization of olefins, to provide components for lubricant and other petrochemical compositions, has been the effective and economic removal of heat of reaction. Expensive refrigeration systems are required to permit polymerization to proceed at preferred temperatures ranging from about 30° to about 100° F. At the higher temperatures, product viscosity decreases markedly. At the desired lower temperatures, the polymerization reaction is more selective for the isobutene in the mixed butene feed.

Existing technology employing aluminum chloride catalyst in a stirred tank requires extensive cooling and also characteristically forms a "red oil" phase which consumes a significant quantity of olefin. The newer technology employing halided alumina, particularly chlorided alumina, in a fixed bed permits operation at temperatures of about 100° F. Refrigeration requirements are less but the yield of desirable polymer tends to be low.

Even though improved polymerization results can be obtained at lower cost employing the halided alumina catalysts, there remains a need for an economically attractive polymerization process for affording high yields of suitable viscous polymer. Particularly attractive would be process conditions requiring no refrigeration, whereby effective cooling could be achieved by the sole use of ambient temperature cooling water.

The known halided alumina catalysts are prepared by heating a gamma-alumina base in the presence of a haliding agent at a temperature within the range from 200° to about 1100° F. One suitable haliding agent comprises about 4 vol. % carbon tetrachloride in a stream of air or argon. By this technique a chloride content of about 6 to 9 wt. % is generated on the catalyst. This technique apparently does not generate aluminum chloride but rather operates to replace oxygen atoms and hydroxyl groups on the alumina surface with halide atoms in a random manner.

SUMMARY OF THE INVENTION

The novel process of this invention provides for the improved preparation of halided alumina catalysts suitable for use in various hydrocarbon conversion processes.

The novel process of this invention particularly provides for the improved manufacture of a high-activity halided alumina catalyst, preferably a chlorided alumina catalyst, for the polymerization of mixed butenes to yield a viscous polymeric product having a viscosity of at least about 15,000 S.S.U. at 210° F.

The novel improvement of this invention comprises the inclusion of a preliminary calcination step conducted in a stream of an inert carrier gas, such as oxygen, whereby the gamma-alumina base is maintained at a temperature within the range from about 1300° to about 1800° F., preferably from about 1350° to about 1650° F., for a time within the range from about 6 to about 16 hours, preferably from about 10 to about 14 hours.

In a preferred embodiment of this invention a chlorided gamma-alumina is prepared under prior art conditions following pre-calcination at a temperature of about 1600° F. for about 14 hours, whereby there is afforded an unexpectedly improved polymerization catalyst for use with isobutene to yield high-viscosity products without need for refrigeration to control the exothermic heat of reaction.

DESCRIPTION OF THE INVENTION

The improvement of this invention makes generally available a high-activity conversion catalyst for selected hydrocarbon reactions, including isomerization, reforming, hydrofining, and the like. More specifically, the high-activity catalyst is a halided alumina catalyst for use primarily in fixed bed reactor systems. In a preferred embodiment the catalyst base is gamma-alumina which has been calcined under selected conditions prior to the conventional haliding step, for eventual use in the improved polymerization of mixed refinery butenes to yield highly viscous polymers.

Generally, halided alumina catalysts, for use in olefin polymerization reactions, are prepared by exposing gamma-alumina to a haliding agent, contained in a minor proportion, usually from about 0.5 to about 10 wt. %, as a vapor in a stream of an inert diluent gas. A commonly employed haliding agent is carbon tetrachloride, often employed at a concentration of about 4 wt. % in air or argon. The chloriding treatment may be effected at a temperature within the range from about 550° to about 1000° F. over a time period within the range from about 1 to about 246 hours. A preferred set of conditions include the use of a temperature of about 650° F. for about 6 hours. This treatment generally will afford a chlorided alumina catalyst containing from about 6 to about 9 wt. % chlorine.

In the polymerization of refinery mixed butene streams, which may contain from about 5 to about 75 wt. %, preferably from about 35 to about 75 wt. %, isobutene, the halided alumina catalyst is employed in a fixed bed system designed for removal of exothermic heat of reaction with less need for refrigerated coolant than with older systems.

The polymeric product, obtained at temperatures ranging from about 30° to about 100° F., comprises a viscous product used in various lubricant formulations as well as in a number of petrochemical products. Generally suitable viscous polymers have a Saybolt viscosity of at least about 15,000 seconds when measured at 210° F. (S.S.U. at 210° F.) At lower polymerization temperatures, the product viscosity is generally greater because of less reaction from normal olefins, so that with mixed butenes the more viscous products more nearly conform to a polyisobutene.

The novel improvement of this invention relates to the surprising effectiveness of a preliminary conditioning step for the gamma-alumina catalyst base. It has now been found that prior calcination of the base at a temperature within the range from about 1300° to about 1800° F. leads to the production of a higher activity halided alumina catalyst than is obtained by any of the prior art techniques. The calcination step of this invention is conducted in a stream of inert gas, such as air or argon. A preferred calcination temperature lies within the range from about 1350° to about 1650° F., more preferably from about 1400° to about 1600° F. The precalcination step of this invention may be continued for a time period within the range from about 6 to about 16 hours, preferably from about 10 to about 14 hours.

It has been surprisingly discovered that the high temperature calcination of this invention results in a two- to three-fold increase in the viscosity of the polymer produced. Even more surprisingly, catalysts prepared by the improved process of this invention make possible the production of commercial grade high molecular weight polymer at temperatures greater than 100° F., whereby effective temperature control can be effected with ambient temperature cooling water. Special refrigeration is rendered unnecessary by the process of this invention.

It has been found that at calcination temperatures of about 1000° F. no improvement is present. At the other extreme, it is well-known that at temperatures approaching 200° F. the catalyst base is converted to the inactive alpha-alumina.

In studies conducted at calcination temperatures of 1400° and 1600° F. and with resultant catalysts employed at temperatures of 80°, 100° and 120° F., respectively, a trend was noted wherein higher product viscosity was associated with greater calcination severity, i.e., longer time or higher temperature.

In a broader aspect, this invention should be applicable for improved catalytic performance in other hydrocarbon conversions requiring catalysts having relatively high acidity.

The following examples are illustrative, without limitation, of the improved process for catalyst preparation disclosed herein.

EXAMPLE A

Gamma-alumina was calcined in a flowing stream of air at a maximum temperature of 1000° F. for 10 hours. A sample of this material was then packed into a reactor, chlorided for 6 hours at 650° F. with a gaseous stream comprising 4 wt. % C Cl4 vapor in air. One-gram portions of the chlorided alumina catalyst were separately employed in the polymerization of a mixture of refinery C4 olefins and paraffins (containing about 45 wt. % isobutene) at temperatures of 80° F., 100° F., and 120° F. After drying the C4 stream using 3A molecular sieves, the feed was pumped at 60–120 psi through a preheater to the fixed-bed reactor. Reactor effluent was recycled to the feed reservoir to provide a continuous loop. Samples of the stream were taken at intervals and analyzed by gel permeation chromatography to obtain the molecular weight distribution. From this, viscosity was calculated, together with the cumulative viscosity at the varying observed degrees of isobutene conversion.

EXAMPLE I

The procedure of Example A was modified to calcine gamma-alumina at 1400° F. for 13 hours. Polymerization of refinery butenes was conducted at 100° F. employing the technique of Example A.

EXAMPLE II

The procedure of Example A was modified to calcine gamma-alumina at 1600° F. for 10 hours. Polymerization of refinery butenes was again conducted at 100° F., according to Example A.

EXAMPLE III

The procedure of Example A was modified to calcine gamma-alumina at 1600° F. for 14 hours, followed by polymerization of refining butenes at 100° F. and 120° F.

Table I presents a summary of data obtained in the performance of the preceding examples. For comparative purposes, viscosities are compared at calculated isobutene conversions of 40 and 80 wt. %. Viscosity data were found to vary linearly with isobutene conversion so that interpolations or extrapolations could be made with confidence.

From Table I it will be noted that pre-treated catalyst III gave surprisingly good (and satisfactory) results even at 120° F. and high isobutene conversion. On the other hand, results with catalyst A (the closest approximation to the prior art) were very poor at 120° F. and borderline at 100° F. Catalysts I and II also gave surprisingly good results.

TABLE I

| Polymerization of Mixed Butenes | | | | | |
|---|---|---|---|---|---|
| | Calcination | | Polymerization | Isobutenene Conversion | Polymer Viscosity | Molecular Weight |
| Catalyst | Temp °F. | Time hrs. | Temp °F. | sion wt. % | SSU @ 210° F. | Mw |
| A | 1000 | 10 | 80 | 40 | 52,500 | 6100 |
| | | | | 80 | 33,000 | 5000 |
| | | | 100 | 40 | 23,000 | 4300 |
| | | | | 80 | 15,000 | 3600 |
| | | | 120 | 40 | 5,000 | 2300 |
| | | | | 80 | 3,000 | 1800 |
| I | 1400 | 13 | 100 | 40 | 32,000 | 5000 |
| | | | | 80 | 19,000 | 4000 |
| II | 1600 | 10 | 100 | 40 | 41,000 | 5500 |
| | | | | 80 | 35,500 | 5200 |
| III | 1600 | 14 | 100 | 40 | 54,500 | 6200 |
| | | | | 80 | 48,500 | 5800 |
| | | | 120 | 40 | 20,500 | 4100 |
| | | | | 80 | 16,000 | 3700 |

I claim:

1. A process for the manufacture of a high-activity chlorided alumina catalyst suitable for olefin polymerization comprising: calcining a catalyst base consisting essentially of gamma alumina at a temperature within the range from about 1300° F. to about 1800° F. for from about 6 to about 16 hours, followed by contacting the calcined catalyst base with a chloriding agent.

2. The process of claim 1 wherein the chloriding agent is carbon tetrachloride, employed at a concentration of about 4 wt. % in air for about 6 hours at a temperature of about 650° F.

3. The process of claim 1 wherein the calcination step is conducted with a flowing stream of an inert gas.

4. The process of claim 3 wherein the inert gas is air.

5. The process of claim 1 wherein the calcination step is conducted at a temperature within the range from about 1350° to about 1650° F.

6. The process of claim 5 wherein the calcination step is conducted at a temperature within the range from about 1400° to about 1600° F.

7. The process of claim 1 wherein the calcination step is conducted for from about 10 to about 14 hours.

* * * * *